United States Patent [19]

Widlund et al.

[11] Patent Number: 5,366,452
[45] Date of Patent: Nov. 22, 1994

[54] METHOD FOR THE FLAT MANUFACTURE OF THREE-DIMENSIONAL ARTICLES, PARTICULARLY ABSORBENT, DISPOSABLE ARTICLES, AND AN ARTICLE PRODUCED IN ACCORDANCE WITH THE METHOD

[75] Inventors: Leif U. R. Widlund, Mölnlycke; Roy Hansson, Mölndal, both of Sweden

[73] Assignee: Mölnlycke AB, Gothenburg, Sweden

[21] Appl. No.: 861,871

[22] PCT Filed: Dec. 14, 1990

[86] PCT No.: PCT/SE90/00838

§ 371 Date: Jun. 19, 1992

§ 102(e) Date: Jun. 19, 1992

[87] PCT Pub. No.: WO91/09580

PCT Pub. Date: Jul. 11, 1991

[30] Foreign Application Priority Data

Dec. 21, 1989 [SE] Sweden .............. 8904317-8

[51] Int. Cl.$^5$ .............. A61F 13/15; A61F 13/20; B65H 81/00; B32B 31/00
[52] U.S. Cl. .............. 604/385.2; 604/358; 604/373; 604/385.1; 156/161; 156/229; 156/496
[58] Field of Search .............. 604/358, 385.1, 385.2, 604/373; 156/161, 163, 164, 229, 496

[56] References Cited

U.S. PATENT DOCUMENTS

| | | | |
|---|---|---|---|
| 4,636,209 | 1/1987 | Lassen | .............. 604/378 |
| 4,642,110 | 2/1987 | Dudek . | |
| 4,735,624 | 4/1988 | Mazars . | |
| 4,775,375 | 10/1988 | Aledo | .............. 604/385.2 |
| 5,151,091 | 9/1992 | Glaug et al. | .............. 604/378 |

FOREIGN PATENT DOCUMENTS

| | | | |
|---|---|---|---|
| 42705/78 | 6/1983 | Australia . | |
| 450454 | 6/1987 | Sweden . | |
| 2041224 | 9/1980 | United Kingdom | .............. 604/378 |
| 2138303 | 10/1984 | United Kingdom | .............. 604/358 |

*Primary Examiner*—Randall L. Green
*Assistant Examiner*—P. Zuttarelli
*Attorney, Agent, or Firm*—Burns, Doane, Swecker & Mathis

[57] ABSTRACT

The present invention relates to a method for the flat manufacture of three-dimensional articles, in particular absorbent disposable articles. According to the invention, a plurality of narrow, flexible absorbent bodies ($1_a$–$1_g$) are placed sequentially on a thin material web of liquid-impermeable material (2; 2') or liquid-permeable material, said pads having mutually diverging side surfaces on both sides of a central pan of said pads intended to form the crotch parts of a manufactured article; placing a thin, second material web of liquid-permeable material (4) or liquid-impermeable material over said bodies and fastening second material web to the first material web (2; 2') so as to enclose each pad between the two material webs; and by rendering those parts of the mutually joined material webs located between the different pads contractable prior to or in conjunction with placing the liquid-permeable material web in position; and by then causing the contractable parts of the material webs to contract and therewith move the side surfaces of the pads towards one another. The invention also relates to an absorbent disposable article manufactured in accordance with the method.

16 Claims, 2 Drawing Sheets

METHOD FOR THE FLAT MANUFACTURE OF THREE-DIMENSIONAL ARTICLES, PARTICULARLY ABSORBENT, DISPOSABLE ARTICLES, AND AN ARTICLE PRODUCED IN ACCORDANCE WITH THE METHOD

BACKGROUND OF THE INVENTION

The present invention relates to a method for the flat manufacture of three-dimensional articles, in particular absorbent disposable articles, and to an article produced in accordance with the method.

Absorbent disposable articles, such as diapers, incontinence guards and sanitary napkins, often consist of a substantially flat absorbent pad enclosed between an outer, liquid-impermeable casing layer and an inner, liquid-permeable casing layer. Such articles are mass produced, by placing absorbent pads on a moving web of material and placing a further web of material on the first mentioned web and fastening the two material webs together in regions thereof which protrude beyond the absorbent pads, whereafter a finished article is cut from the thus formed composite web. In the case of the present document, this article is considered to be flat. The human bodies on which such articles are worn, however, are anything but flat and consequently when the article is put on, the absorbent pad will deform and form folds and pleats in the article. Furthermore, it is difficult to shape such articles so that they conform to the shape of the user's body when worn. These factors contribute to an impaired function of the article, particularly with respect to leakage reliability.

If this deformation and folding of absorbent, disposable articles could be eliminated or reduced and/or controlled, the risk of leakage with such articles would be reduced to a significant extent. A large number of different constructions are known whose primary purpose is to avoid the formation of folds in sensitive regions of the article, for instance at the margins or edges of the crotch region of the article, or to provide controlled deformation of the article, for instance so that raised embankments or flaps are formed along the edge margins of the crotch part of the article. It is also known to provide such articles with patterns of pre-tensioned elastic threads or bands, so as to impart a basin-like shape to the article or parts thereof.

SUMMARY

An object of the present invention is to solve the aforesaid problems encountered with absorbent, disposable articles, by providing an article which can be manufactured in a flat state and which, subsequent to manufacture, will assume a three-dimensional shape corresponding to the shape of the user's body.

To this end, there is proposed in accordance with the invention a method of the aforesaid kind which is characterized by placing a plurality of flat, flexible pads intended to form the three-dimensional article sequentially on a flat support surface, such that the side surfaces of at least some mutually adjacent pads will diverge from one another over at least certain sections of the bodies, and by mutually joining the side surfaces of said pads with the aid of pre-stretched contractable devices, and by subsequently permitting the devices to contract so as to convert the article from a flat state to a three-dimensional shape.

The invention also relates to an absorbent, disposable article, such as a diaper, an incontinence guard or a sanitary napkin, manufactured in accordance with said method and comprising an absorbent pad or body enclosed between an inner and an outer casing layer. The inventive article is characterized in that the absorbent body is constructed from a plurality of elongated narrow bodies, each of which is enclosed between two casing layers which are mutually joined along parts lying externally of said bodies; and in that the side surfaces of said bodies are joined, or substantially joined, to the side surfaces of adjacent bodies at least in those parts which lie outside the crotch region of the article; and in that the article has a three-dimensional shape.

So that the invention will be more readily understood and further features thereof made apparent, the invention will now be described in more detail with reference to an exemplifying embodiment thereof illustrated in the accompanying drawings, in which

DETAILED DESCRIPTION OF THE PREFERRED EMBODIMENT

Figure 1:
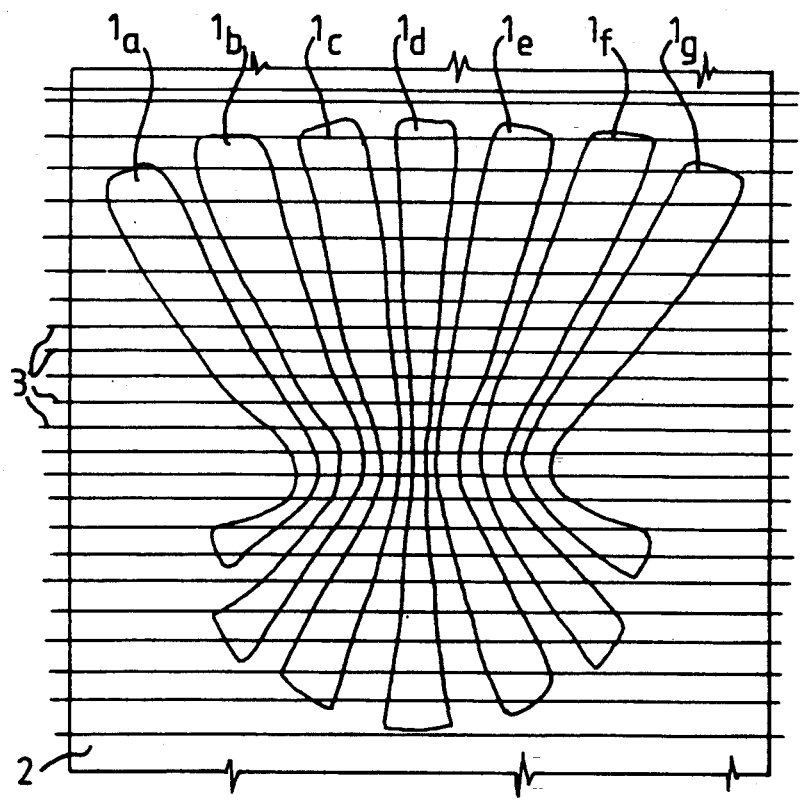
FIG. 1 illustrates one stage in the inventive manufacture of a first embodiment of an inventive diaper.

FIG. 1 illustrates the step in the manufacture of an inventive diaper prior to applying a liquid-permeable casing layer. As shown in the Figure, the absorbent pad of the diaper is comprised of a number of elongated, narrow flat bodies $1_a$–$1_g$ made of an absorbent material, for instance cellulose fluff, which may be admixed with so-called superabsorbents and/or melt fibres. In the case of the FIG. 1 embodiment, the bodies $1_a$–$1_g$ have been placed, in a first manufacturing step, on a web of liquid-impermeable material 2 in the pattern illustrated in FIG. 1, said liquid-impermeable material forming an outer casing layer or backing sheet of the finished article. A plurality of transverse, stretched elastic threads 3 have then been placed on the bodies $1_a$–$1_g$ in a second manufacturing step.

The stage of manufacture illustrated in FIG. 1 has now been reached. In order to obtain a finished diaper from the configuration illustrated in FIG. 1, all that remains is to apply a web of liquid-permeable material 4 (not shown in FIG. 1) such as to form an inner casing layer of the finished article, and to secure this material web to the material web 2 in regions lying outside the bodies $1_a$–$1_g$, and attach fastener tabs 5 (not shown in FIG. 1) and then cut the finished article from the composite web. The material webs are preferably joined together with the aid of glue coated on one or on both of said webs over the whole of its surface or over parts thereof.

When the article is cut from the composite web, the elastic threads 3 will contract in those parts which lie outside the bodies $1_a$–$1_g$. No appreciable contraction of the elastic threads will take place in those parts of the threads which extend over the bodies $1_a$–$1_g$, owing to the stiffness or rigidity of these bodies. Thus, those parts of the mutually joined, thin casing layers 2, 4 located between the bodies $1_a$–$1_g$ will be folded or pleated between said bodies and the side surfaces of said bodies will be moved towards one another.

As will be seen from FIG. 1, the adjacent side surfaces of the bodies $1_a$–$1_g$ will diverge away from one another on both sides of a central transverse part which forms the crotch part of the diaper in use. This means that the bodies are forced to curve out of the plane illustrated in FIG. 1 (the plane of the paper) in order for the side surfaces to be brought towards one another. It will be seen that if the side surfaces are straight, the joining line will also be straight and lie in a plane which is inclined to the original plane of the bodies. When the side surfaces are composed along their lengths from straight parts with varying directions, it will be seen that the joining line will extend in a plurality of mutually different inclined planes. It will also be seen against this background that if the side surfaces are curved between said parts of varying directions, the joining line will also be curved between its straight parts, while if the side edges are arcuate in their entirety, the joining line will also be arcuate.

Figure 2:
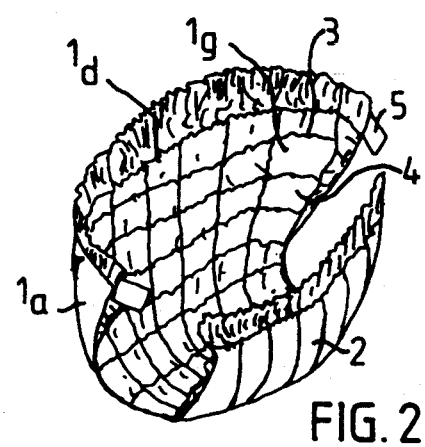
FIG. 2 shows the diaper of FIG. 1 when manufacture is completed.

FIG. 2 illustrates the diaper of FIG. 1 in its final state. Thus, it will be seen that a diaper whose shape corresponds to the shape of a baby's or child's bottom can be produced by appropriate configuration of the bodies or pads $1_a$–$1_g$ and appropriate positioning of said bodies or pads in relation to one another.

Figure 3:
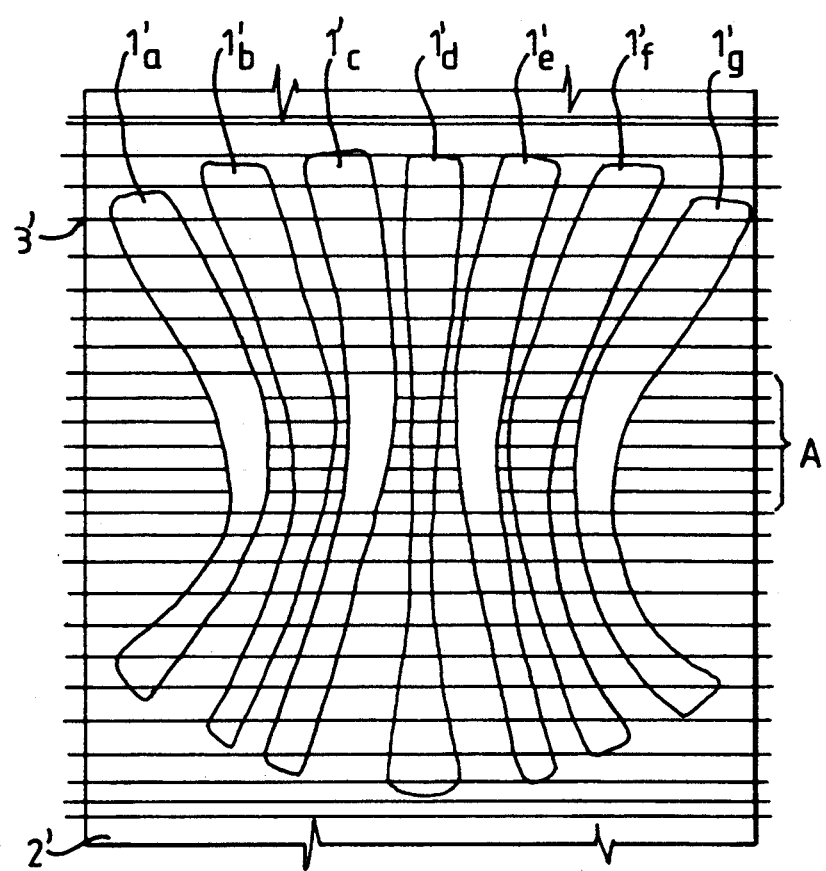
FIG. 3 illustrates the same step as that in FIG. 1 in the manufacture of a diaper according to another embodiment of the invention.

FIG. 3 illustrates the same manufacturing step as that shown in FIG. 1 but in connection with a second embodiment of an inventive diaper. This embodiment differs from the embodiment according to FIGS. 1 and 2, in that the bodies $1'_a$, $1'_c$ and $1'_g$ have been placed on top of the elastic threads $3'$ within the region A.

This is achieved by first placing the bodies $1'_b$, $1'_d$ and $1'_f$ onto the material web $2'$ and then placing the threads $3'$ located within the region A, which corresponds to the crotch region of a finished diaper, on top of said bodies. The remaining bodies $1'_a$, $1'_c$, $1'_e$ and $1'_g$ and the remainder of the elastic threads $3'$ are then placed in position. In other respects, the manufacture of the diaper according to this second embodiment of the invention is effected in the same manner as that described with reference to the diaper illustrated in FIGS. 1 and 2.

The elastic threads $3'$ present within the crotch part of a thus manufactured diaper will strive to bring together the upper and lower edges of the side surfaces of adjacent bodies, whereas the elastic threads $3'$ in remaining parts of the diaper will strive to bring together the upper sides of the side surfaces of adjacent bodies. Thus, the elastic threads in the crotch part of the diaper will strive to bring the bodies $1'_b$, $1'_d$ and $1'_f$ to a lower level than the bodies $1'_a$, $1'_c$, $1'_e$ and $1'_g$. This is made possible because the bodies located within the crotch part of the diaper can be displaced into mutually overlapping relationship when putting the diaper onto a child wearer. This affords two important advantages. The first advantage is that the bodies $1'_a$–$1'_g$ can be made wider in the crotch part of the diaper than would otherwise be the case, therewith increasing the strength of the diaper in the region thereof subjected to the heaviest loads in use, while the second advantage is that more absorbent material can be used in that part of the diaper where most liquid collects. Furthermore, the dispersion of liquid from the crotch part is improved with a diaper of this configuration, since more bodies or pads are active in this liquid dispersion process.

It will be understood that an elastic casing material can be used instead of elastic threads for the purpose of rendering the outwardly lying parts of the casing materials contractable. One particularly suitable material in this regard is film having a so-called elastic memory, for instance different types of Exxon Extraflex, i.e. a plastic material which can be greatly extended under plastic deformation, so that its extension will remain subsequent to removing the load but which when subsequently heated will return to its original size and therewith possess elastic properties within the region between its original size and its extended size. Shrink film or combinations of shrink film and elastic material are also conceivable for use in providing contractable parts.

It is in this respect pointed out that the elasticity of the finished diaper is primarily intended to enable the diaper to fit the bottoms of children of different sizes, and to form waist elastication.

When the invention is applied in the manufacture of three-dimensional absorbent disposable articles, there is obtained, in addition to the aforesaid good properties with respect to leakage reliability and shape conformity, which are conducive with the three-dimensional shape, the further advantage of decreasing the risk of the absorbent bodies lumping together, this advantage being conducive with the division of the absorbent body or pad into several, mutually separate bodies or pads. Furthermore, any lumping together of an inventive absorbent pad will present less of a problem than the same occurrence in a conventional absorbent pad, since the lumping together of a separate inventive pad will not influence the longitudinal dispersion of liquid in adjacent pads.

It will be understood that the illustrated embodiments can be modified in several ways within the scope of the invention, particularly with regard to the shape of the bodies and the kind of article in which the invention is applied. Furthermore, in other applications of the invention than those of the exemplifying embodiments, the separate pads can be placed closer together than in the pattern illustrated in FIG. 1, in which inter-spaces between the pads must always be present in order to enable the pads to swell when absorbing liquid. It will also be understood that the invention can be solely applied in the manufacture of the backing piece of a diaper, which is then secured to a separate front piece manufactured in a conventional manner, since the front piece of the diaper when worn will have a substantially flat form. The invention is, therefore, solely restricted to the content of the following claims.

What is claimed is:

1. An absorbent disposable article having a crotch region, comprising:
   an inner casing layer;
   an outer casing layer;
   an absorbent body having a longitudinal and a transverse direction enclosed between said inner and said outer casing layers;
   said absorbent body including a plurality of elongated, narrow, and flexible absorbent bodies having longitudinally extending edge surfaces, the bodies disposed in a transverse adjacent relationship, a longitudinally intermediate part of the absorbent body forming a crotch region;
   each of said elongated bodies being enclosed between said two casing layers;
   said two casing layers being mutually joined at parts which lie externally of said elongated bodies;
   contractable means for substantially joining together the longitudinally extending edge surfaces of said elongated bodies, at least in parts which lie outside the crotch region of the article, to opposing longitudinally extending edge surfaces of adjacent bodies;

said contractable means being attached to at least one of said casing layers; and the article having a three-dimensionally curved configuration.

2. The article according to claim 1, wherein the casing layers are elastic in parts which lie between said absorbent bodies, at least in parts of the article which lie outside the crotch region of said article.

3. The article according to claim 2, wherein the casing layers include intermediate elastic bands, which are mounted in a stretched state and which extend transversally from one side of the article to the other on top of the elongated absorbent bodies in parts of the article which lie externally of the crotch region and extend alternately over and under the bodies within the crotch region of said article.

4. A method for manufacturing a three-dimensional curved article, comprising the steps of:

placing on a planar support surface having a longitudinal and transverse direction a plurality of flat, flexible, elongated absorbent bodies in transverse side-by-side relationship, each of said bodies having in a planar state longitudinally extending edge surfaces which diverge transversely outward on both sides of an intermediate part of each body from a reference plane extending longitudinally through a group center of said plurality of elongated bodies;

mutually connecting said bodies by connecting stretched means over said bodies and spaces between said bodies, said stretched means being contractable transversely to the longitudinal direction of said flat elongated bodies; and causing said stretched means to contract to bring said bodies towards one another so as to convert the article from a flat state to a three-dimensional curved configuration.

5. The method according to claim 4, wherein said longitudinal edge surfaces diverge from the reference plane only in certain sections thereof.

6. A method for manufacturing an absorbent disposable article of three-dimensionally curved configuration, comprising the steps of:

placing on a planar thin first material web of material having a longitudinal and a transverse direction a plurality of elongated, narrow and flexible absorbent bodies in a transverse side-by-side relationship, each of said bodies having in a planar state an intermediate part between opposed end parts and longitudinal extending edge surfaces which diverge transversely outward on both sides of the intermediate part of each body from a reference plane extending longitudinally through a group center of said plurality of elongated bodies;

placing a thin second material web of material over said bodies and fastening said second material web to said first material web so as to enclose each body between the two material webs;

rendering parts of the mutually joined material webs located between said bodies contractable; and causing the contractable parts of the material webs to contract, thereby to move adjacent longitudinal extending edge surfaces of the bodies towards one another so as to convert the absorbent article from said planar state to a three-dimensional curved configuration, whereby said intermediate parts of said bodies form a crotch part of said article.

7. The method according to claim 6, wherein the longitudinal extending edge surfaces of the elongated bodies are placed in spaced relationship with the longitudinal extending edge surfaces of adjacent bodies over a whole longitudinal length of said bodies.

8. The method according to claim 6, wherein said first material web is liquid impermeable.

9. The method according to claim 6, wherein said first material web is liquid permeable.

10. The method according to claim 6, wherein said second material web is liquid impermeable.

11. The method according to claim 6, wherein said second material web is liquid permeable.

12. The method according to claim 6, wherein said rendering step occurs prior to placing the second material web in position.

13. The method according to claim 6, wherein said rendering step occurs in conjunction with placing the second material web in position.

14. The method according to claim 6, wherein the longitudinal extending edge surfaces of the bodies are mutually joined to the longitudinal extending edge surfaces of adjacent bodies by prestretched elastic material.

15. The method according to claim 14, wherein the prestretched elastic material comprises a film possessing an elastic memory.

16. The method according to claim 14, wherein said prestretched elastic material is a shrink film.

* * * * *